United States Patent [19]

Bruderer et al.

[11] Patent Number: 4,766,115
[45] Date of Patent: Aug. 23, 1988

[54] 5,6-DIHDRO-6H-DIBENZ(C,E)AZEPINE-6-(THIO)CARBOXIMIDIC ACID ESTERS AND INSECTICIDAL USE THEREOF

[75] Inventors: Hans Bruderer, Biel-Benken; René Zurflüh, Bülach, both of Switzerland

[73] Assignee: Hoffmann-La Roche Inc., Nutley, N.J.

[21] Appl. No.: 816,511

[22] Filed: Jan. 6, 1986

[30] Foreign Application Priority Data

Jan. 10, 1985 [CH] Switzerland .................. 95/85
Oct. 28, 1985 [CH] Switzerland .................. 4629/85

[51] Int. Cl.$^4$ .................. A01N 47/42; C07D 223/18
[52] U.S. Cl. .................. 514/217; 540/587
[58] Field of Search .................. 260/229 D; 540/592, 540/587; 514/213, 217

[56] References Cited

U.S. PATENT DOCUMENTS 3,017,337 1/1962 Spiegelberg et al. .......... 260/239 D
3,055,883 4/1982 Mull .......................... 260/239 D
3,116,283 12/1963 Boller et al. ................ 260/239 D

FOREIGN PATENT DOCUMENTS 61-161266 7/1986 Japan ........................ 514/217
373757 1/1964 Switzerland ................ 540/587

Primary Examiner—Glennon H. Hollrah
Assistant Examiner—D. B. Springer
Attorney, Agent, or Firm—Jon S. Saxe; George M. Gould; Dennis P. Tramaloni

[57] ABSTRACT

The invention is concerned with novel heterocyclic compounds of the formula

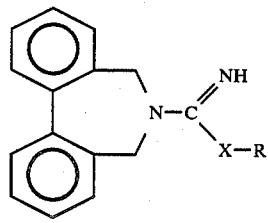

I wherein R is $C_{1-12}$-alkyl, $C_{3-12}$-alkenyl, $C_{3-12}$-alkynyl or $C_{3-8}$-cycloalkyl and X signifies oxygen or sulfur, and none of the possible multiple bonds of R is present in the α-position to X, and their acid addition salts, processes for their manufacture, insect control compositions which contain these compounds as the active substance as well as the use of such compounds or compositions for the control of insects. Moreover, the invention is concerned with starting materials used for the preparation of such compounds.

22 Claims, No Drawings

5,6-DIHYDRO-6H-DIBENZ(C,E)AZEPINE-6-(THIO)-CARBOXIMIDIC ACID ESTERS AND INSECTICIDAL USE THEREOF

DETAILED DESCRIPTION OF THE INVENTION

The present invention is concerned with heterocyclic compounds, namely 5,7-dihydro-6H-dibenz[c,e]azepine-6-(thio)carboximidic acid esters of the formula

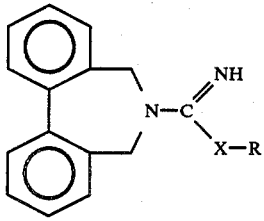

I wherein
R is $C_{1-12}$-alkyl, $C_{3-12}$-alkenyl, $C_{3-12}$-alkynyl or $C_{3-8}$-cycloalkyl and
X is oxygen or sulfur,
and none of the possible multiple bonds of R is present in the α-position to X,
as well as acid addition salts of these compounds.

The compounds in accordance with the invention, i.e. the compounds of formula I and their acid addition salts, are pest control agents and are especially suitable for the control of insects and mites, e.g. spider mites. Accordingly, the invention also embraces pest control compositions which contain compounds in accordance with the invention as the active substance, processes for the preparation of these compounds as well as methods of use of these compounds or compositions for the control of pests.

The $C_{1-12}$-alkyl, $C_{3-12}$-alkenyl and $C_{3-12}$-alkynyl residues mentioned in the above definition of the compounds of formula I can be not only straight-chain but also branched. Moreover, the $C_{3-12}$-alkenyl and $C_{3-12}$-alkenyl residues can have one or more double or triple bonds, respectively.

Where asymmetric carbon atoms are present in the compounds of formula I, the compounds occur in optically active form. In the case of those compounds of formula I in which R is $C_{3-12}$-alkenyl geometric isomerism can additionally occur. Formula I is accordingly intended to embrace all of these possible isomeric forms as well as their mixtures, e.g. racemic mixtures.

As acid addition salts of the compounds of formula I there come into consideration physiologically compatible salts. Hereto there belong salts of these compounds with inorganic and organic acids, preferably hydrohalic acids such as hydrochloric acid and hydrobromic acid; nitric acid; phosphoric acid; sulfuric acid; mono- and bifunctional carboxylic acids and hydroxycarboxylic acids such as acetic acid, maleic acid, succinic acid, fumaric acid, tartaric acid, citric acid, salicylic acid, sorbic acid and lactic acid; and sulfonic acids such as 1,5-naphthalene-disulfonic acid.

Independently of each other R is preferably $C_{1-12}$-alkyl, especially $C_{1-3}$-alkyl, and X is preferably oxygen. Especially preferred compounds of formula I are:
Ethyl 5,7-dihydro-6H-dibenz[c,e]azepine-6-carboximidate and its hydrochloride,
methyl 5,7-dihydro-6H-dibenz[c,e]azepine-6-carboximidate and its hydrochloride,
propyl 5,7-dihydro-6H-dibenz[c,e]azepine-6-carboximidate and its hydrochloride and
isopropyl 5,7-dihydro-6H-dibenz[c,e]azepine-6-carboximidate and its hydrochloride.

The compounds of formula I and their acid addition salts in accordance with the invention are prepared by the processes described below:

(a) Reacting 5,7-dihydro-6H-dibenz[c,e]azepine-6-carbonitrile, i.e. the cyanamide of the formula

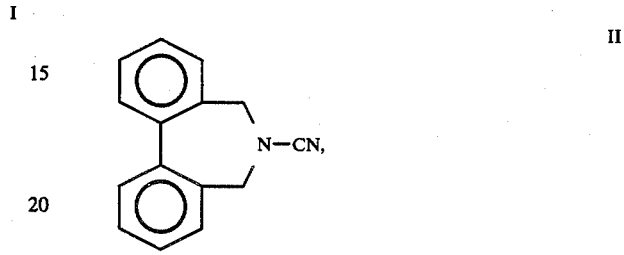

II with an alcohol or thiol of the formula

R—XH                   III wherein R and X are as defined above, or with an alkali metal salt thereof.

The reaction according to procedure (a) is conveniently carried out using excess alcohol or thiol of formula III as the solvent and in the presence of a catalytic or stoichiometric amount of an alkali metal salt, especially the sodium or potassium salt, of the alcohol or thiol of formula III. In a further embodiment there are used the alcohol or the thiol of formula II as the reactant and one equivalent of alkali metal cyanide, especially sodium or potassium cyanide. The reaction temperatures can be varied in a wide range, generally from 10° to 80° C., preferably from 20° to 60° C.

(b) For the preparation of those compounds of formula I in which R is methyl or ethyl, alkylating a urea or thiourea of the formula

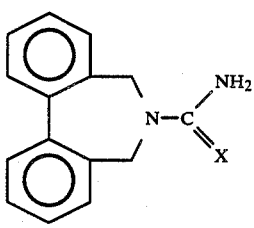

IV wherein X is as defined above.

The alkylation according to procedure (b) is conveniently carried out using trimethyl- or triethyloxonium tetrafluoroborate, preferably employing one equivalent of this reagent and preferably is a chlorinated hydrocarbon such as methylene chloride or chloroform as the solvent. The reaction temperatures conveniently lie between 0° and 40° C., preferably between 20° and 25° C. The thus-formed salt of the compound of formula I can be converted into the free thiocarboximidic acid ester by treatment with a base, preferaly sodium carbonate in aqueous solution, in a conventional manner.

Insofar as no planned synthesis for the isolation of pure isomers is carried out, a product which exists as two or more isomers is obtained as a mixture of these isomers. The isomers can be separated according to methods well known to those skilled in the art, or, if desired, they can also be prepared e.g. by synthesis from corresponding optically active starting materials.

If desired, a compound of formula I obtained by procedure (a) or (b) can be converted into an acid addition salt by reaction with the corresponding acid. The compounds I are reacted with the desired acids in the usual manner, for example by dissolving the compound of formula I in a suitable solvent and adding the acid thereto.

The isolation and the purification of the prepared compounds of formula I or of the acid addition salts can be carried out according to methods well known to those skilled in the art.

The cyanamide of formula II which is used as the starting material in procedure (a) is novel and forms a further object of the present invention. This starting material can be prepared, for example, by
(a′) reacting a compound of the formula

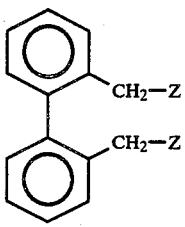

V wherein Z is a leaving group such as halogen (preferably chlorine or bromine), mesyloxy or tosyloxy, with the disodium or calcium salt of cyanamide in an alcohol, e.g. ethanol, or with cyanamide itself in the presence of dimethyl sulphoxide-sodium in dimethyl sulphoxide, or with cyanamide in the presence of 50% sodium hydroxide solution, a water-immiscible inert solvent such as an aromatic, e.g. benzene or toluene, an aliphatic or cyclic ether, e.g. tert.butyl methyl ether, or a halogenated hydrocarbon, e.g. methylene chloride, and a phase-transfer catalyst such as tricaprylmethylammonium chloride or tetrabutylammonium chloride.

In this procedure the reaction temperatures can be varied in a wide range such as between 20° C. and the reflux temperature of the reaction mixture. The compounds of formula V are, in turn, either known or can be produced from 2,2′-biphenylmethanol according to methods well known in the art.

The starting material of formula II can also be prepared according to the following procedures.

(b′) Reacting 6,7-dihydro-5H-dibenz[c,e]azepine with a cyanogen halide, preferably cyanogen chloride or cyanogen bromide, at low temperatures, preferably −5° to 10° C., in an inert solvent such as an aliphatic or cyclic ether, an aromatic or a halogenated hydrocarbon, e.g. chloroform.

(c′) Treating a urea or thiourea of formula IV with an excess amount of chloroform and 50% sodium hydroxide solution in the presence of a phase-transfer catalyst, preferably a tertiary amine such as triethylamine, at room temperature and while stirring, whereby water or hydrogen sulphide as the case may be is eliminated from the N-substituent of IV.

Additional procedures for the preparation of the starting material of formula II are based on the methods generally described in Houben-Weyl, Methoden der Organischen Chemie, vol. VIII, pages 172-177.

The starting materials of formula IV are also novel and form a further object of the present invention. They can be prepared, for example, by heating 6,7-dihydro-5H-dibenz[c,e]azepine with urea or thiourea to 130°-150° C. or by reacting the azepine hydrochloride with potassium cyanate or thiocyanate at a slightly elevated temperature, preferably at 50°-80° C. These methods are well known in the art, e.g. from Houben-Weyl, Methoden der Organischen Chemie, vol. VIII, pages 149-157. 5,7-Dihydro-6H-dibenz[c,e]azepine-6-carboxamide is an especially preferred starting material of formula IV.

The isolation and the purification of the thus-produced starting materials can be carried out according to procedures well known in the art.

The compounds of formula I are quite generally of value as pesticides. They have been shown to be especially valuable for the control of mites and insects, especially of mites which are of importance in plant protection such as e.g.

Tetranychidae (spider mites), especially *Tetranychus urticae, Tetranychus cinnabarinus, Tetranychus turkestani, Tetranychus McDanieli, Tetranychus kanzawai;*

*Panonychus ulmi, Panonychus citri;*

*Phyllocoptruta oleivora;*

*Aculus schlechtendali;*

*Phyllocoptes vitis;*

*Aceria essigi, Aceria gracilis;*

*Cecidophyopsis ribis:*

*Eriophyes vitis, Eriophyes sheldoni, Eriophyes tulipae;*

*Eotetranychus sexmaculatus, Eotetranychus carpini;*

*Hemitarsonemus latus;*

*Acarus siro;*

*Bryobia graminum;* mites which are of importance in veterinary medicine such as e.g.

*Macronyssus bursa, Macronyssus sylviarum, Macronyssus lacoti;*

*Dermanyssus gallinae;* ticks, especially of the families Ixodidae and Argasidae and of the orders Boophilus, Amblyomma, Hyalomma, Rhipicephalus, Ixodes, Argas and Ornithodorus.

The compounds in accordance with this invention act as contact and feed poisons. Moreover, some of the compounds are taken up by various plants, so that the pests to be controlled are killed when they eat the plants. These compounds thus exhibit systemic activity.

The pest control composition in accordance with the invention contains an effective amount of at least one compound of formula I, as defined above, or an acid addition salt of such a compound as well as formulation adjuvants. The composition conveniently contains at least one of the following formulation adjuvants:

Solid carrier substances; solvents or dispersion media; tensides (wetting and emulsifying agents); dispersing agents (without tenside action); and stabilizers.

With the use of these and, if desired, additional adjuvants the compounds of formula I, namely the pesticidally active substances, can be converted into the usual formulations such as solutions, suspensions, emulsions, emulsifiable concentrates, pastes, foams, dusts, powders and granulates.

As solid carrier substances there essentially come into consideration: natural mineral substances such as kaolin, aluminas, siliceous earth, talc, bentonite, chalk, limestone, quartz, dolomite, attapulgite, montmorillonite and diatomaceous earth; synthetic mineral substances such as highly dispersible silicic acid, aluminum oxide and silicates; organic substances such as cellulose, starch, urea and synthetic resins; and fertilizers such as phosphates and nitrates, whereby such carrier substances can be present e.g. as dusts, powders or granulates.

As solvents or dispersion media there essentially come into consideration: aromatics such as toluene, xylenes, benzene and alkylnaphthalenes; chlorinated aromatics and chlorinated aliphatic hydrocarbons such as chlorobenzenes, chloroethylenes and methylene chloride; aliphatic hydrocarbons such as cyclohexane and paraffins, e.g. petroleum fractions; alcohols such as butanol and glycol as well as their ethers and esters; ketones such as acetone, methyl ether ketone, methyl isobutyl ketone and cyclohexanone; and strongly polar solvents such as dimethylformamide N-methylpyrrolidone and dimethyl sulphoxide, such solvents or dispersion media preferably having flash points of at least 30° C. and boiling points of at least 50° C., and water. As solvents or dispersion media there also come into consideration so-called liquified gaseous extenders or carrier substances, namely products which are gaseous at room temperature and under normal pressure. Examples of such products are especially aerosol propellants such as halogenated hydrocarbons, e.g. dichlorodifluoromethane. When water is used as the solvent, organic solvents can e.g. also be used as auxiliary solvents.

The tensides (wetting and emulsifying agents) can be non-ionic compounds such as condensation products of fatty acids, fatty alcohols or fatty-substituted phenols with ethylene oxide; fatty acid esters and ethers of sugars or polyvalent alcohols; the products which are obtained from sugars or polyvalent alcohols by condensation with ethylene oxide; block polymers of ethylene oxide and propylene oxide; or alkyldimethylamine oxides.

The tensides can also be anionic compounds such as soaps; fatty sulphate esters, e.g. dodecyl sodium sulphate, octadecyl sodium sulphate and cetyl sodium sulphate; alkyl sulphonates, aryl sulphonates and fatty-aromatic sulphonates such as alkylbenzene sulphonates, e.g. calcium dodecylbenzenesulphonate, and butylnaphthalene sulphonates; and more complex fatty sulphonates, e.g. the amide condensation products of oleic acid and N-methyltaurine and the sodium sulphonate of dioctyl succinate.

Finally, the tensides can be cationic compounds such as alkyldimethylbenzylammonium chlorides, dialkyldimethylammonium chlorides, alkyltrimethylammonium chlorides and ethoxylated quaternary ammonium chlorides.

As dispersing agents (without tenside action) there essentially come into consideration: lignin, sodium and ammonium salts of lignin sulphonic acids, sodium salts of maleic anhydride-diisobutylene copolymers, sodium and ammonium salts of sulphonated polycondensation products of naphthalene and formaldehyde, and sulphite lyes.

As dispersing agents, which are especially suitable as thickening or anti-settling agents, there can be used e.g. methylcellulose, carboxymethylcellulose, hydroxyethylcellulose, polyvinyl alcohol, alginates, caseinates and blood albumin.

Examples of suitable stabilizers are acid-binding agents, e.g. epichlorohydrin, phenyl glycidyl ether and soya epoxides; antioxidants, e.g. gallic acid esters and butylhydroxytoluene; UV-absorbers, e.g. substituted benzophenones, diphenylacrylonitrile acid esters and cinnamic acid esters; and deactivators, e.g. salts of ethylenediaminotetraacetic acid and polyglycols.

The pest control compositions in accordance with the invention can contain, in addition to the active substances of formula I, other active substances, e.g. other pest control agents, pest baits, fungicides, bactericides, plant growth regulators and fertilizers. Such combination compositions are suitable for intensifying the activity or for broadening the spectrum of activity. If desired, insufficiencies of hitherto known added agents can thereby also be compensated for.

It has been found that the compounds I in accordance with the invention, especially the particularly preferred compound ethyl 5,7-dihydro-6H dibenz[c,e]azepine-6-carboximidate and its hydrochloride, are used with advantage in combination with conventional acaricides, especially with conventional acaricides which are suitable for the control of eggs and larvae of mites. Examples of such acaricides are chlorbenside, chlorfenson, clofentezine, fenson, fenothiocarb, flubenzimine, tetradifon, hexythiazox, benzoximate, amitraz, dienochlor and 4-pent-4-ynyloxyphenyl phenyl ether as well as 1,2,4-triazoles having acaricidal activity such as, for example, 3-(o-chlorophenyl)-1-methyl-5-(o-trifluoromethyl-phenyl)-1H-1,2,4-triazole. The use can be carried out simultaneously or separately. Thereby, the active substances in accordance with the invention can compensate for the disadvantage of known acaricides having a main focus of activity against the eggs and larvae, in that the mobile stages which survive after the use of these known acaricides and which can develop rapidly into a new pest population are also killed. Since eggs, various larval stages as well as adults, namely male and female forms, often appear simultaneously under practical conditions, an overall effect which is extremely suitable in practice, i.e. more rapid, more effective and longer-lasting, can be achieved with combination preparations. However, the total amount of the two active substances in such combination preparations conveniently amounts to not more than the amount of active substance when a compound I is used as the sole active substance.

The pest control compositions in accordance with the invention contain, according to type, between 0.005 and 95 weight percent of the compound or compounds in accordance with the invention as the active substance. They can be present in a form which is suitable for storage and transport. In such forms, e.g. emulsifiable concentrates, the active substance concentration is normally in the higher region of the above concentration range. These forms can be diluted with the same or different formulation adjuvants to give active substance concentrations which are suitable for practical use and such concentrations normally lie in the lower region of the above concentration range. Emulsifiable concentrates generally contain 5 to 90 weight percent, preferably 10 to 80 weight percent, of the compound(s) in accordance with the invention. As forms of use there come into consideration, inter alia, ready-for-use solutions, emulsions, suspensions, foams, powders, pastes, dusting compositions and granulates. The active substance concentrations in such ready-for-use compositions can be varied in wide limits. In spray liquors there can be present e.g. concentrations between 0.005 and 0.5 weight percent. In the Ultra-Low-Volume process there can be formulated spray liquors in which the active substance concentration is preferably from 10 to 20 weight percent, while the spray liquors formulated in the Low-Volume process and in the High-Volume process preferably have an active substance concentration of 0.01 to 0.5 and 0.005 to 0.1 weight percent, respectively. Granulates preferably contain from 5 to 50 weight percent of the compound(s) in accordance with the invention as the active substance.

The pest control compositions in accordance with the invention can be manufactured by mixing at least one compound of formula I or an acid addition salt of such a compound with formulation adjuvants.

The manufacture of the compounds can be carried out using conventional techniques, e.g. by mixing the active substance with solid carrier substances, by dissolution or suspension in suitable solvents or dispersion media, if necessary using tensides as wetting or emulsifying agents, or dispersing agents, by diluting pre-prepared emulsifiable concentrates with solvents or dispersion media, etc.

In the case of pulverous compositions the active substance can be mixed with a solid carrier substance, e.g. by grinding together; or the solid carrier substance can be impregnated with a solution or suspension of the active substance and then the solvent or suspension medium can be removed by evaporation, by heating or by filtering-off under reduced pressure. By adding tensides or dispersing agents such pulverous compositions can be made readily wettable with water, so that they can be converted into aqueous suspensions which are suitable e.g. as spray compositions.

The compounds of formula I or their acid addition salts can also be mixed with a tenside and a solid carrier substance to form a wettable powder which is dispersible in water or they can be mixed with a solid granulated carrier substance to form a granulate.

If desired, the compound of formula I or an acid addition salt thereof can be dissolved in a water-immiscible solvent such as, for example, an alicyclic ketone, which conveniently contains a dissolved emulsifying agent, so that the solution becomes self-emulsifying upon addition to water. Alternatively, the active substance can be mixed with an emulsifying agent and the mixture can then be diluted with water to the desired concentration. Moreover, the active substance can be dissolved in a solvent and thereafter the solution can be mixed with an emulsifying agent. Such a mixture can likewise be diluted with water to the desired concentration. In this manner there are obtained emulsifiable concentrates or ready-for-use emulsions.

The method in accordance with the invention for the control of pests comprises treating the locus to be protected or the pests themselves with an effective amount of a compound in accordance with the invention or of a pest control composition in accordance with the invention. This method of use can be carried out by application to the soil or leaves or by application to the animals, supplies or materials to be protected, depending on the kind of pests to be controlled. The control is achieved, for example, by contact or by intake with the feed.

The use can be carried out in a conventional manner, e.g. by sprinkling, spraying, atomising, dusting, scattering, drilling-in, smoking, watering, steeping or coating. Pulverous preparations can be applied to the pests or to the locus to be protected, e.g. plants or animals, as e.g. dusting agents with the aid of the usual dusting appliances. Aqueous suspensions can be used e.g. as spray compositions.

When used in plant protection a dosage of about 100–500 g of active substance [compound(s) of formula I]/ha is usually sufficient, e.g. as is the case in the application of 2000 l of spray liquor which contains 0.005–0.025 weight percent of active substance to 1 ha of cultivated land.

The following Examples serve to illustrate the invention in more detail.

I. PREPARATION OF THE ACTIVE INGREDIENTS OF FORMULA I

Example 1

1.5 g of 5,7-dihydro-6H-dibenz[c,e]azepine-6-carbonitrile are added to a solution of sodium methylate in methanol prepared from 0.16 g of sodium and 20 ml of absolute methanol, and the mixture is heated to reflux temperature for 1 hour. The solvent is subsequently distilled off, the residue is treated with water and the resulting aqueous mixture is extracted three times with methylene chloride. The combined extracts are washed with water, dried over anhydrous sodium sulphate and evaporated. In this manner there is obtained methyl 5,7-dihydro-6H-dibenz[c,e]azepine-6-carboximidate as an oil.

The above product is dissolved in a small amount of alcohol and the solution is treated with 1.4 ml of a 5N alcoholic hydrochloric acid solution. 20 ml of n-hexane are then added thereto, and the precipitated product is filtered off under suction and recrystallized from alcohol. There is obtained pure methyl 5,7-dihydro-6H-dibenz[c,e]azepine-6-carboximidate hydrochloride, m.p. 205°–208° C.

In an analogous manner, starting from 5,7-dihydro-6H-dibenz[c,e]azepine-6-carbonitrile and sodium ethylate in ethanol there is obtained ethyl 5,7-dihydro-6H-dibenz[c,e]azepine-6-carboximidate and therefrom with hydrochloric acid in alcohol there is obtained the hydrochloride, m.p. 158° C. (with decomposition);

starting from 5,7-dihydro-6H-dibenz[c,e]azepine-6-carbonitrile and sodium ethanethiolate in ethanethiol there is obtained ethyl 5,7-dihydro-6H-dibenz[c,e]azepine-6-thiocarboximidate and therefrom with hydrochloric acid in alcohol there is obtained the hydrochloride, m.p. 220° C. (with decomposition);

starting from 5,7-dihydro-6H-dibenz[c,e]azepine-6-carbonitrile and sodium propylate in n-propanol there is obtained propyl 5,7-dihydro-6H-dibenz[c,e]azepine-6-carboximidate and therefrom with hydrochloric acid in alcohol there is obtained the hydrochloride, m.p. 147° C. (with decomposition);

starting from 5,7-dihydro-6H-dibenz[c,e]azepine-6-carbonitrile and sodium isopropylate in isopropanol there is obtained isopropyl 5,7-dihydro-6H-dibenz[c,e]azepine-6-carboximidate and therefrom with hydrochloric acid in alcohol there is obtained the hydrochloride, m.p. 158° C. (with decomposition);

starting from 5,7-dihydro-6H-dibenz[c,e]azepine-6-carbonitrile and sodium dodecanethiolate in 1-dodecanethiol there is obtained dodecyl 5,7-dihydro-6H-dibenz[c,e]azepine-6-thiocarboximidate, which is purified by flash chromatography on silica gel using n-hexane/ethyl acetate (1:1) as the eluent; $^1$H-NMR(CDCl$_3$): 0.88 (t, C$\underline{H}_3$), 1.2–2.0 (20H), 2.5 (t, SC$\underline{H}_2$), 4.43 (s, 4H), 7.3–7.7 (8H);

starting from 5,7-dihydro-6H-dibenz[c,e]azepine-6-carbonitrile and sodium 2-butanethiolate in 2-butanethiol there is obtained 2-butyl 5,7-dihydro-6H-dibenz[c,e]azepine-6-thiocarboximidate which is purified by flash chromatography on silica gel using n-hexane/ethyl acetate (1:1) as the eluent, $^1$H-NMR(CDCl$_3$): 1.05 (t, C$\underline{H}_2$CH$_3$), 1.42 (d, CH—C$\underline{H}_3$), 1.46–1.93 (m, C$\underline{H}_2$CH$_3$), 2.81–3.37 (m, 1H), 4.41 (s, 4H), 5.1 (broad s, N$\underline{H}$), 7.37–7.70 (8H).

Example 2

A mixture of 1.99 g of 5,7-dihydro-6H-dibenz[c,e]azepine-6-carbonitrile, 0.59 g of potassium cyanide and 20 ml of allyl alcohol is stirred at room temperature for 20 hours and thereafter the allyl alcohol is distilled off. The residue is poured onto ice/water and extracted with methylene chloride, and the combined extracts are washed with water, dried over anhydrous sodium sulphate and evaporated. After flash chromatography on silica gel (elutent: ethyl acetate) there is obtained pure allyl 5,7-dihydro-6H-dibenz[c,e]azepine-6-carboximidate as an oil.

The above product is dissolved in 2.5 ml of methanol, the solution is cooled to 0° C. and treated with 1.3 ml of a 5N alcoholic hydrochloric acid solution. After stirring for 15 minutes 10 ml of n-hexane are added and the precipitated product is then filtered off under suction. There is obtained allyl 5,7-dihydro-6H-dibenz[c,e]azepine-6-carboximidate hydrochloride, m.p. 115° C. (with decomposition).

In an analogous manner, starting from 5,7-dihydro-6H-dibenz[c,e]azepine-6-carbonitrile and n-butanol there is obtained butyl 5,7-dihydro-6H-dibenz[c,e]azepine-6-carboximidate as a resinous product, $^1$H-NMR(CDCl$_3$): 1.02 (t, CH$_2$C$\underline{H}_3$), 1.4–2.0 (4H), 4.15 (t, OC$\underline{H}_2$), 4.27 (s, 4H), 4.57 (broad s, N$\underline{H}$), 7.3–7.7 (8H);

starting from 5,7-dihydro-6H-dibenz[c,e]azepine-6-carbonitrile and 2-butanol there is obtained 2-butyl 5,7-dihydro-6H-dibenz[c,e]azepine-6-carboximidate as a resinous product, $^1$H-NMR(CDCl$_3$): 1.02 (t, CH$_2$C$\underline{H}_3$), 1.35 (d, CH—C$\underline{H}_3$), 1.4–2.0 (m, 2H), 4.23 (s, 4H), 4.83 (m, 1H), 7.3–7.7 (8H);

starting from 5,7-dihydro-6H-dibenz[c,e]azepine-6-carbonitrile and isobutanol there is obtained isobutyl 5,7-dihydro-6H-dibenz[c,e]azepine-6-carboximidate as a resinous product, $^1$H-NMR(CDCl$_3$): 1.07 [d, C$\underline{H}$(CH$_3$)$_2$], 2.1 (m, 1H), 3.95 (d, C$\underline{H}_2$), 4.25 (s, 4H), 4.55 (broad s, N$\underline{H}$), 7.3–7.7 (8H);

starting from 5,7-dihydro-6H-dibenz[c,e]azepine-6-carbonitrile and 1-octanol there is obtained octyl 5,7-dihydro-6H-dibenz[c,e]azepine-6-carboximidate as a resinous product, $^1$H-NMR(CDCl$_3$): 0.88 (t, C$\underline{H}_3$), 1.0–2.0 (12H), 4.15 (t, OC$\underline{H}_2$), 4.23 (s, 4H), 4.87 (broad s, N$\underline{H}$), 7.3–7.7 (8H);

starting from 5,7-dihydro-6H-dibenz[c,e]azepine-6-carbonitrile and propargyl alcohol there is obtained 2-propynyl 5,7-dihydro-6H-dibenz[c,e]-6-caboximidate as a resinous product, $^1$H-NMR(CDCl$_3$): 2.51 (t, C$\underline{H}$) 4.2 (s, 4H), 4.41 (broad s, N$\underline{H}$), 4.87 (d, OC$\underline{H}_2$), 7.3–7.7 (8H);

starting from 5,7-dihydro-6H-dibenz[c,e]azepine-6-carbonitrile and cyclohexanol there is obtained cyclohexyl 5,7-dihydro-6H-dibenz[c,e]azepine-6-carboximidate as a resinous product, $^1$H-NMR(CDCl$_3$): 1.1–2.3 (10H), 4.21 (s, 4H), 4.75 (m, OC$\underline{H}$), 4.95 (broad s, N$\underline{H}$), 7.3–7.7 (8H);

starting from 5,7-dihydro-6H-dibenz[c,e]azepine-6-carbonitrile and cyclohexanol there is obtained cyclohexyl 5,7-dihydro-6H-dibenz[c,e]azepine-6-carboximidate as a syrup, $^1$H-NMR(CDCl$_3$): 1.5–2.1 (8H), 4.2 (s, 4H), 4.67 (broad s, N$\underline{H}$), 5.1 (m, OC$\underline{H}$), 7.3–7.7 (8H).

Example 3

5 g of 5,7-dihydro-6H-dibenz[c,e]azepine-6-carbonitrile in 60 ml of absolute alcohol are heated to reflux temperature for 1 hour in the presence of 30 mg of sodium ethylate. After distilling off the alcohol the residue is treated with water and the mixture is extracted three times with methylene chloride. The combined extracts are washed with water, dried over anhydrous sodium sulphate and evaporated, and the residue is distilled in a bulb-tube oven at 230°–250° C./0.1 mmHg. There is obtained ethyl 5,7-dihydro-6H-dibenz[c,e]azepine-6-carboximidate as a clear resin which becomes solid; m.p. 68°–71° C.

Example 4

1.19 g of 5,7-dihydro-6H-dibenz[c,e]azepine-6-carboxamide are dissolved in 10 ml of methylene chloride, and the solution is treated with 1.14 g of triethyloxonium tetrafluoroborate and stirred at room temperature for 20 hours. The mixture is then poured on to 10% sodium carbonate solution/ice and the whole is extracted with methylene chloride. The combined extracts are washed with 10% sodium carbonate solution, dried over anhydrous sodium sulphate and evaporated under reduced pressure. In this manner there is obtained crude ethyl 5,7-dihydro-6H-dibenz[c,e]azepine-6-caboximidate which is purified by a filtration on silica gel [eluent: n-hexane/ethyl acetate (1:1)]; m.p. 74°–76° C. (crystallized from n-hexane).

Example 5

A solution of 0.68 g of oxalic acid in 6 ml of alcohol is added dropwise to a solution of 1.0 g of ethyl 5,7-dihydro-6H-dibenz[c,e]azepine-6-carboximidate in 8 ml of benzene. The solution is stirred for a further 15 minutes, the solvent is subsequently distilled off and the residue is crystallized from ethanol/diethyl ether. After recrystallization from a small amount of ethanol there are obtained white crystals of ethyl 5,7-dihydro-6H-dibenz[c,e]azepine-6-carboximidate 1.5 oxalate, m.p. 120° C. (with decomposition). [The addition of 1.5 equivalents of oxalic acid is indicated by elementary analysis of the product.]

Example 6

1 ml of concentrated phosphoric acid is added dropwise to an ice-cold solution of 1 g of ethyl 5,7-dihydro-6H-dibenz[c,e]azepine-6-carboximidate in diethyl ether. After distilling of the solvent the initially oily product is crystallized from alcohol/benzene, and there are obtained after recrystallization from a small amount of alcohol white crystals of ethyl 5,7-dihydro-6H-dibenz[c,e]azepine-6-carboximidate diphosphate, m.p. 154° C. (with decomposition). [The addition of 2 equivalents of phosphoric acid is indicated by elementary analysis of the product.]

In an analogous manner, starting from ethyl 5,7-dihydro-6H-dibenz[c,e]azepine-6-carboximidate and concentrated sulphuric acid there is obtained 5,7-dihydro- 6H-dibenz[c,e]azepine-6-carboximidate sulphate as white crystals, m.p. 146° C. (with decomposition; crystallized from methanol).

II. PREPARATION OF THE STARTING MATERIAL OF FORMULA II

Example 7

180 ml of 50% sodium hydroxide solution are treated at about 60° C. in sequence with 7.7 g of cyanamide, 1.3 g of tricaprylmethylammonium chloride, 360 ml of benzene and 62 g of 2,2'-bis(bromomethyl)-biphenyl, and the mixture is stirred at 60°-70° C. for 6 hours. After cooling the reaction mixture this is transferred to a separating funnel and shaken with 50 ml of methylene chloride, whereby the separated product is taken up in the methylene chloride phase. The aqueous phase is back-extracted twice with methylene chloride. The combined extracts are subsequently washed with water, dried over anhydrous sodium sulphate and evaporated, and the residue is taken up in 100 ml of toluene and the solution is heated to reflux temperature, filtered and treated at about 50° C. with 200 ml of tert.-butyl methyl ether. Finally, the crystals which are precipitated by ice-cooling are filtered off under suction and dried. In this manner there is obtained pure 5,7-dihydro-6H-dibenz[c,e]azepine-6-carbonitrile, m.p. 121°-124° C.

Example 8

A solution of 1.91 g of cyanogen bromide in 20 ml of chloroform is added dropwise at 5°-10° C. within 25 minutes to a solution, cooled to 5° C., of 7 g of 6,7-dihydro-5H-dibenz[c,e]azepine in 50 ml of chloroform. The reaction mixture is stirred for a further 1 hour and then a small amount of the hydrobromide salt of the still unreacted azepine is filtered off. The filtrate is washed three times with water, dried over anhydrous sodium sulphate and evaporated. There is obtained solid 5,7-dihydro-6H-dibenz[c,e]azepine-6-carbonitrile, m.p. 123°-126° C.

Example 9

A mixture of 1.19 g of 5,7-dihydro-6H-dibenz[c,e]azepine-6-carboxamide (see Example 10), 12 ml of chloroform, 2.7 ml of 50% sodium hydroxide solution and 50 mg of triethylamine is stirred at room temperature for 1 hour. The reaction mixture is then poured onto ice/water and the whole is extracted with methylene chloride. The extracts are washed with water, dried over anhydrous sodium sulphate and evaporated, and the residue is purified by flash chromatography on silica gel [eluent: n-hexane/ethyl acetate (9:1)]. There is obtained 5,7-dihydro-6H-dibenz[c,e]azepine-6-carbonitrile, m.p. 118°-121° C.

III. PREPARATION OF THE STARTING MATERIALS OF FORMULA IV

Example 10

A mixture of 1.95 g of 6,7-dihydro-5H-dibenz[c,e]azepine and 3 g of urea is stirred at 120° C. for 15 minutes and then poured onto ice/water. After extracting the resulting aqueous mixture with methylene chloride the combined extracts are washed with water, dried over anhydrous sodium sulphate and evaporated. The solid residue is recrystallized from n-hexane/ethyl acetate, and in this manner there is obtained pure 5,7-dihydro-6H-dibenz[c,e]azepine-6-carboxamide, m.p. 212°-214° C.

IV. FORMULATION EXAMPLES

Example 11

A spray powder has the following composition:

| | Weight percent |
| --- | --- |
| Compounds of formula I or acid addition salt thereof (active ingredient) | 50 |
| Hydrated silicic acid (carrier substance) | 37 |
| Polycarboxylic acid sodium salt (dispersing agent) | 4 |
| Nonylphenyl-(10)ethoxylate (wetting agent) | 4 |
| Kaolin (carrier substance) | 5 |
| | 100 |

The active ingredient is mixed with the kaolin and separately the wetting agent is taken up on the hydrated silicic acid and the dispersing agent is added. The whole is then mixed homogeneously and finely ground in a suitable mill. The thus-obtained spray powder is spontaneously wetted by water and in this manner gives a ready-for-use dispersion.

Example 12

An emulsifiable concentrate has the following composition:

| | g/liter |
| --- | --- |
| Compound of formula I (active ingredient) | 250 |
| Polyarylphenol-(18)ethoxylate (emulsifier) | 300 |
| Isoterdecyl alcohol (antifoam agent) | 20 |
| Polyvinylpyrrolidine (dispersing agent) | 20 |
| N—methyl-pyrrolidine (solvent) ad | 1000 ml |

The active ingredient, the emulsifier and the antifoam agent are taken up in the solvent while stirring. Thereupon, the dispersing agent is added and dissolved while stirring. After dilution with water the thus-obtained emulsifiable concentrate gives an emulsion which is well suited as a ready-for-use spray liquor.

What is claimed is:

1. A compond of the formula

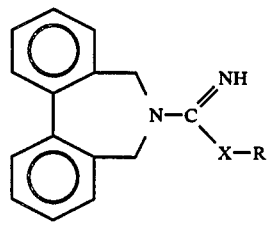

I wherein
R is $C_{1-12}$-alkyl, $C_{3-12}$-alkenyl, $C_{3-12}$-alkynyl or $C_{3-8}$-cycloalkyl and
X is oxygen or sulfur, and none of the possible multiple bonds of R is present in the α-position to X, as well as acid addition salts of these compounds.

2. The compound according to claim 1, wherein R is $C_{1-3}$-alkyl.

3. The compound according to claim 1, wherein X is oxygen.

4. Ethyl 5,7-dihydro-6H-dibenz[c,e]azepine-6-carboximidate and its hydrochloride.

5. Methyl 5,7-dihydro-6H-dibenz[c,e]azepine-6-carboximidate and its hydrochloride.

6. Propyl 5,7-dihydro-6H-dibenz[c,e]azepine-6-carboximidate and its hydrochloride.

7. Isopropyl 5,7-dihydro-6H-dibenz]c,e]azepine-6-carboximidate and its hydrochloride.

8. A compound according to claim 1, selected from the group consisting of
ethyl 5,7-dihydro-6H-dibenz[c,e]azepine-6-thiocarboximidate and its hydrochloride,
dodecyl 5,7-dihydro-6H-dibenz[c,e]azepine-6-thiocarboximidate,
2-butyl 5,7-dihydro-6H-dibenz[c,e]azepine-6-thiocarboximidate,
allyl 5,7-dihydro-6H-dibenz[c,e]azepine-6-carboximidate and its hydrochloride,
butyl 5,7-dihydro-6H-dibenz[c,e]azepine-6-carboximidate,
2-butyl 5,7-dihydro-6H-dibenz[c,e]azepine-6-carboximidate,
isobutyl 5,7-dihydro-6H-dibenz[c,e]azepine-6-carboximidate,
octyl 5,7-dihydro-6H-dibenz[c,e]azepine-6-carboximidate,
2-propynyl 5,7-dihydro-6H-dibenz[c,e]azepine-6-carboximidate,
cyclohexyl 5,7-dihydro-6H-dibenz[c,e]azepine-6-carboximidate,
cyclopentyl 5,7-dihydro-6H-dibenz[c,e]azepine-6-carboximidate,
ethyl 5,7-dihydro-6H-dibenz[c,e]azepine-6-caboximidate 1.5 oxalate and
ethyl 5,7-dihydro-6H-dibenz[c,e]azepine-6-carboximidate diphosphate.

9. A composition for the control of insects comprising an effective amount of at least one compound of the formula

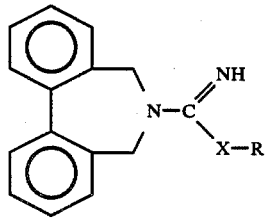

I wherein
R is $C_{1-12}$-alkyl, $C_{3-12}$-alkenyl, $C_{3-12}$-alkynyl or $C_{3-8}$-cycloalkyl
and
X is oxygen or sulfur,
and none of the possible multiple bonds of R is present in the α-position to X,
or an acid addition salt thereof, as well as formulation adjuvants.

10. The insect control composition according to claim 9, comprising an effective amount of at least one compound selected from the group consisting of
ethyl 5,7-dihydro-6H-dibenz[c,e]azepine-6-carboximidate and its hydrochloride,
methyl 5,7-dihydro-6H-dibenz[c,e]azepine-6-carboximidate and its hydrochloride,
propyl 5,7-dihydro-6H-dibenz[c,e]azepine-6-carboximidate and its hydrochloride and
isopropyl 5,7-dihydro-6H-dibenz[c,e]azepine-6-carboximidate and its hydrochloride as well as formulation adjuvants.

11. The insect control composition according to claim 9, which contains as an additional active substance an acaricide for the control of undeveloped stages of mites, namely of the eggs and larvae.

12. A method for the control of insects, which method comprises treating the locus to be protected or the insects themselves with an effective amount of a compound in accordance with claim 1.

13. A method for the control of insects, which method comprises treating the locus to be protected or the insects themselves with an effective amount of a compound in accordance with claim 2.

14. A method for the control of insects, which method comprises treating the locus to be protected or the insects themselves with an effective amount of a compound in accordance with claim 3.

15. A method for the control of insects, which method comprises treating the locus to be protected or the insects themselves with an effective amount of a compound in accordance with claim 4.

16. A method for the control of insects, which method comprises treating the locus to be protected or the insects themselves with an effective amount of a compound in accordance with claim 5.

17. A method for the control of insects, which method comprises treating the locus to be protected or the insects themselves with an effective amount of a compound in accordance with claim 6.

18. A method for the control of insects, which method comprises treating the locus to be protected or the insects themselves with an effective amount of a compound in accordance with claim 7.

19. A method for the control of insects, which method comprises treating the locus to be protected or the insects themselves with an effective amount of a compound in accordance with claim 8.

20. A method for the control of insects, which method comprises treating the locus to be protected or the insects themselves with an effective amount of a composition in accordance with claim 9.

21. A method for the control of insects, which method comprises treating the locus to be protected or the insects themselves with an effective amount of a composition in accordance with claim 10.

22. A method for the control of insects, which method comprises treating the locus to be protected or the insects themselves with an effective amount of a composition in accordance with claim 11.

* * * * *

UNITED STATES PATENT AND TRADEMARK OFFICE
CERTIFICATE OF CORRECTION

PATENT NO. : 4,766,115
DATED : August 23, 1988
INVENTOR(S) : Hans Bruderer and Rene Zurfluh It is certified that error appears in the above-identified patent and that said Letters Patent is hereby corrected as shown below:

title page at [54]

"5,6-DIHDRO-6H-DIBENZ(C,E)AZEPINE-6-(THIO)CARBOXIMIDIC ACID ESTERS AND INSECTICIDAL USE THEREOF" should be "5,7-DIHYDRO-6H-DIBENZ[C,E]AZEPINE-6-(THIO)CARBOXIMIDIC ACID ESTERS AND INSECTICIDAL USE THEREOF".

Signed and Sealed this

Ninth Day of October, 1990

*Attest:*

HARRY F. MANBECK, JR.

*Attesting Officer*      *Commissioner of Patents and Trademarks*